United States Patent [19]
Mihashi et al.

[11] Patent Number: 6,042,233
[45] Date of Patent: Mar. 28, 2000

[54] OPTICAL CHARACTERISTIC MEASURING APPARATUS

[75] Inventors: Toshifumi Mihashi; Katsuhiko Kobayashi, both of Tokyo, Japan

[73] Assignee: Kabushiki Kaisha Topcon, Tokyo, Japan

[21] Appl. No.: 09/190,842

[22] Filed: Nov. 12, 1998

[30] Foreign Application Priority Data

Nov. 11, 1997 [JP] Japan .................................. 9-327098

[51] Int. Cl.[7] .......................................................... A61B 3/10
[52] U.S. Cl. ........................................................... 351/221
[58] Field of Search .................................... 351/205, 206, 351/211, 213, 216, 220, 221, 219, 246

[56] References Cited

U.S. PATENT DOCUMENTS

| | | | |
|---|---|---|---|
| 5,537,164 | 7/1996 | Smith ...................................... | 351/219 |
| 5,576,780 | 11/1996 | Yancey ..................................... | 351/211 |
| 5,623,323 | 4/1997 | Johnson et al. ........................... | 351/219 |

*Primary Examiner*—George Manuel
*Attorney, Agent, or Firm*—Baker Botts, L.L.P.

[57] ABSTRACT

Disclosed is an optical characteristic measuring apparatus for precisely measuring optical characteristics of an eye to be examined by projecting a specific pattern on the retina of the eye. In particular, the measuring apparatus is capable of measuring an irregular astigmatism component. In this apparatus, an illuminating optical system illuminates the retina of an eye to be examined via an illuminating state changing unit capable of changing an illuminating state created by light rays emitted from the light source; a light receiving optical system receives light rays reflected back from the retina of the eye and guides the reflected light rays to a light receiving unit; and an optical characteristic arithmetic unit determines optical characteristics of the eye on the basis of a signal outputted from the light receiving unit. The above illuminating state changing unit changes, on the basis of the optical characteristics obtained by the optical characteristic arithmetic unit, the illuminating state of the illuminating optical system such that the illuminating optical system illuminates a minute region on the retina of the eye.

7 Claims, 13 Drawing Sheets

FIG. 3
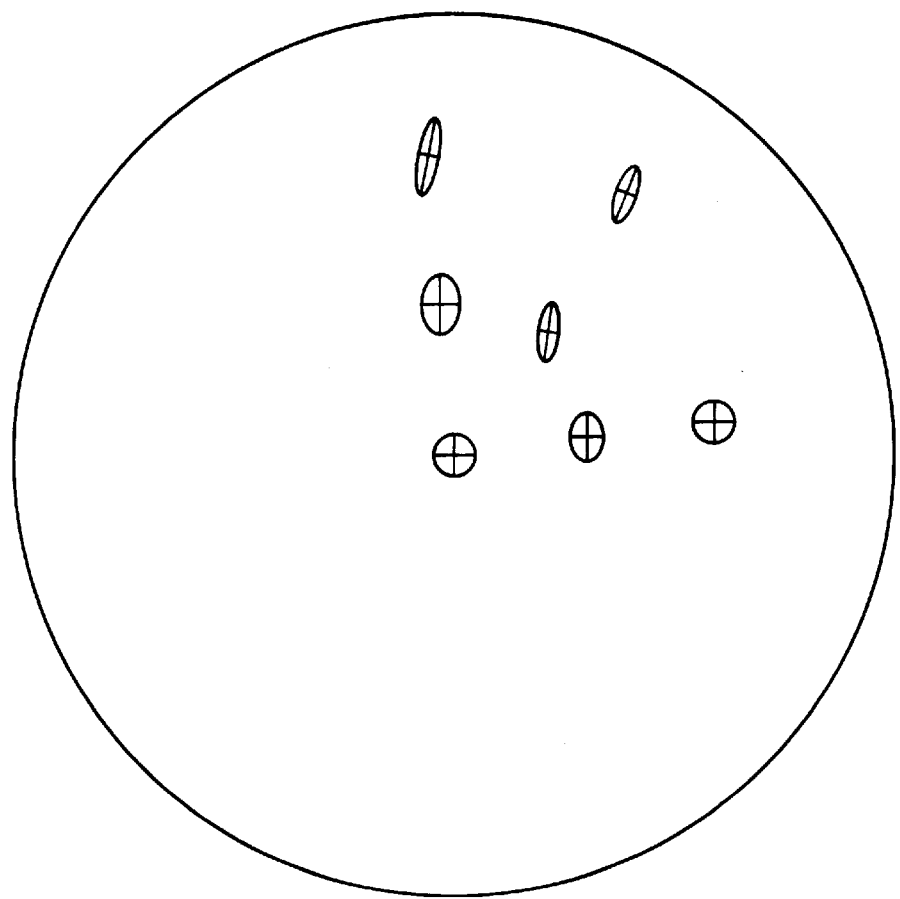
ELLIPSES INDICATE MAXIMUM POWER, MINIMUM POWER,
THE DIRECTION OF MAXIMUN POWER AND THE DIRECTION
OF MINIMUM POWER

REGULAR ASTIGMATISM

IRREGULAR ASTIGMATISM

OBJECTIVE LENSES 301
LIGHT RECEIVING SCREEN 500
OBJECT TO BE EXAMINED
MOVABLE LENSES 302
100 LIGHT SOURCE
400 HARTMANN PLATE

OBJECT TO BE EXAMINED IS CONJUGATE WITH LIGHT RECEIVING SCREEN

CASE OF LENS METER

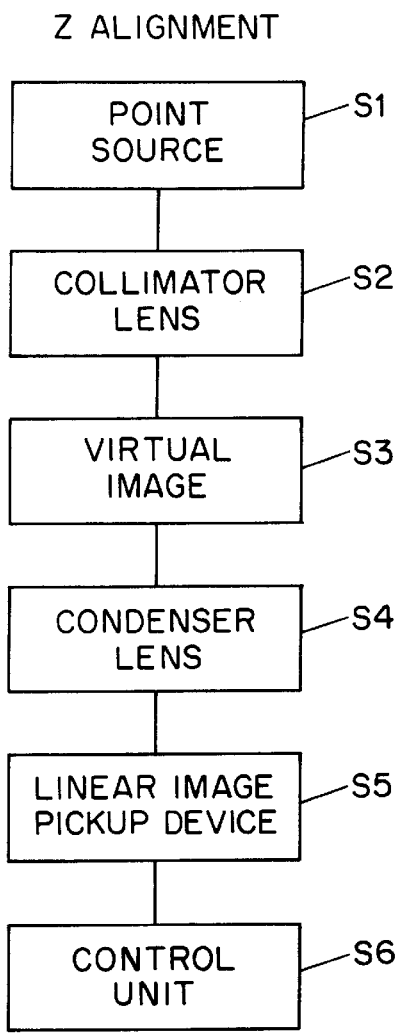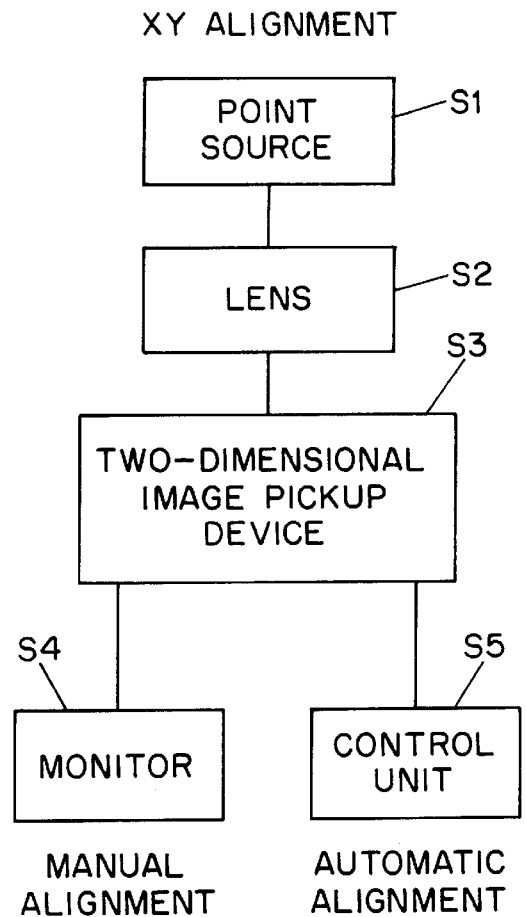

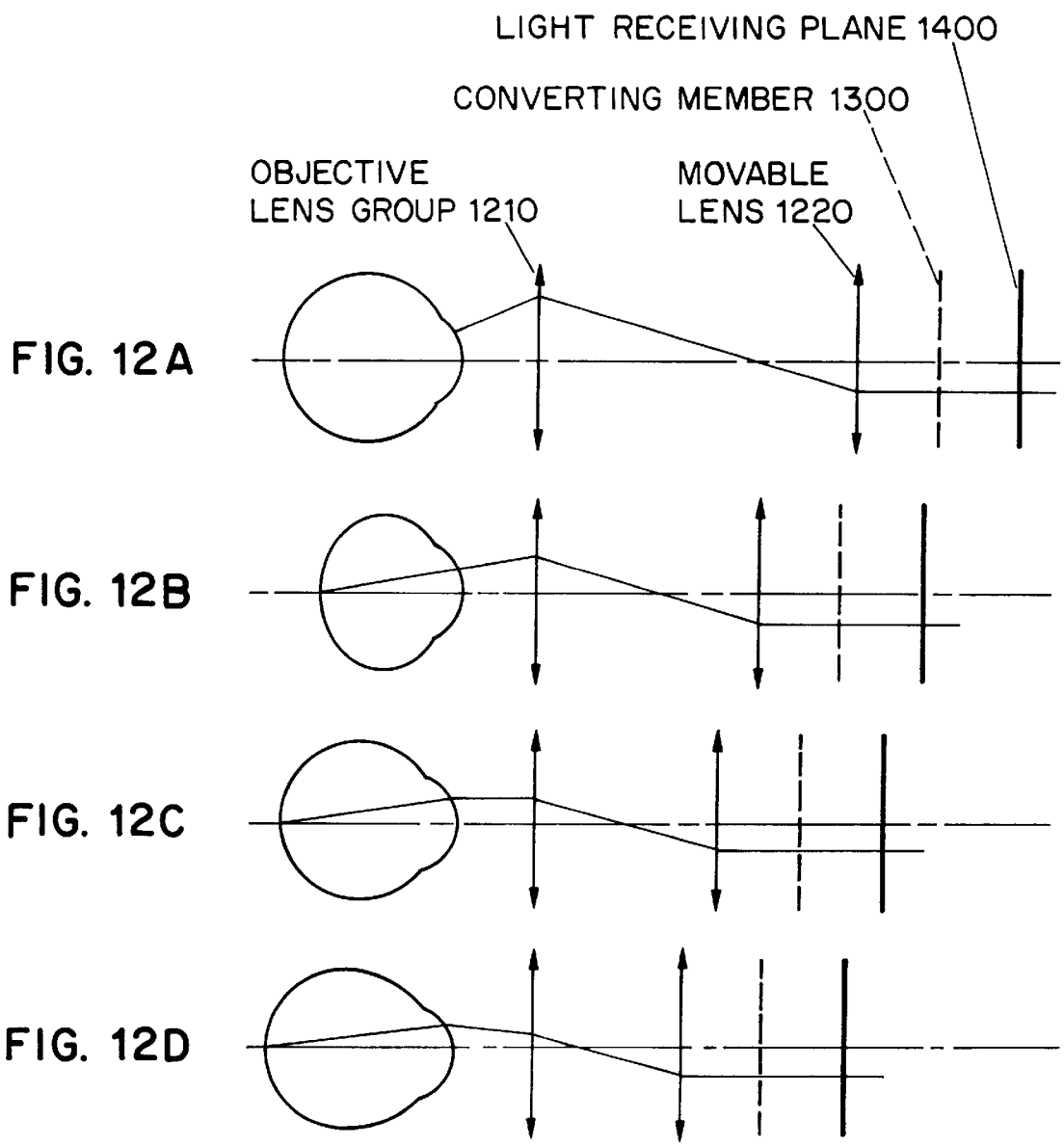

OPTICAL CHARACTERISTIC MEASURING APPARATUS

BACKGROUND OF THE INVENTION

The present invention relates to an optical characteristic measuring apparatus for precisely measuring optical characteristics of an eye to be examined by projecting a specific pattern on the retina of the eye, and particularly to an optical characteristic measuring apparatus capable of measuring optical characteristics of an irregular astigmatism component of the eye.

A prior art apparatus for measuring optical characteristics of an eye to be examined, known as a refractometer, is capable of expressing the optical characteristics of the eye merely as a spherical component, a regular astigmatism component and the angle of the axis of the regular astigmatism component. Some eyes have an irregular astigmatism component in addition to a regular astigmatism component. If the quantity of the irregular astigmatism component is large, such an irregular astigmatism may be required to be corrected by use of a set of contact lenses instead of a pair of spectacles or through examination of the eye by a medical doctor.

While the present applicant has developed an optical characteristic measuring apparatus with consideration given to the irregular astigmatism component and filed the patent application thereof, such an apparatus has a problem that if an eye to be examined is not in emmetropia, an index point cannot be projected as a point image on the eyeground of the eye by the effect of the astigmatism component or the like, tending to cause a measurement error.

In view of the foregoing, it has been strongly needed to develop an optical characteristic measuring apparatus capable of forming a specific pattern on the retina of an eye to be examined even if the eye has regular and irregular astigmatism components.

SUMMARY OF THE INVENTION

An object of the present invention is to provide an optical characteristic measuring apparatus for precisely measuring optical characteristics of an eye to be examined by projecting a specific pattern on the retina of the eye, and particularly, an optical characteristic measuring apparatus capable of measuring an irregular astigmatism component. To achieve the above object, according to an aspect of the present invention, there is provided an optical characteristic measuring apparatus including an illuminating optical system, a light receiving optical system, and an optical characteristic arithmetic unit. The illuminating optical system illuminates the retina of an eye to be examined via an illuminating state changing unit capable of changing an illuminating state created by light rays emitted from the light source. The light receiving optical system receives light rays reflected back from the retina of the eye and guides the reflected light rays to a light receiving unit. The optical characteristic arithmetic unit determines optical characteristics of the eye on the basis of a signal outputted from the light receiving unit. The above illuminating state changing unit changes, on the basis of the optical characteristics obtained by the optical characteristic arithmetic unit, the illuminating state of the illuminating optical system such that the illuminating optical system illuminates a minute region on the retina of the eye.

BRIEF DESCRIPTION OF THE DRAWINGS

FIG. 3 is a diagrammatic view of assistance in explaining a method of directly indicating power based on quantity and orientation relating to maximum curvature and minimum curvature;

FIG. 10 is a block diagram illustrating XY alignment;

FIG. 11 is a block diagram illustrating Z alignment;

FIG. 12 is a diagram illustrating alignment; and

DESCRIPTION OF THE INVENTION

Hereinafter, embodiments of the present invention will be described with reference to the accompanying drawings.

[First Embodiment]

Figure 1A:
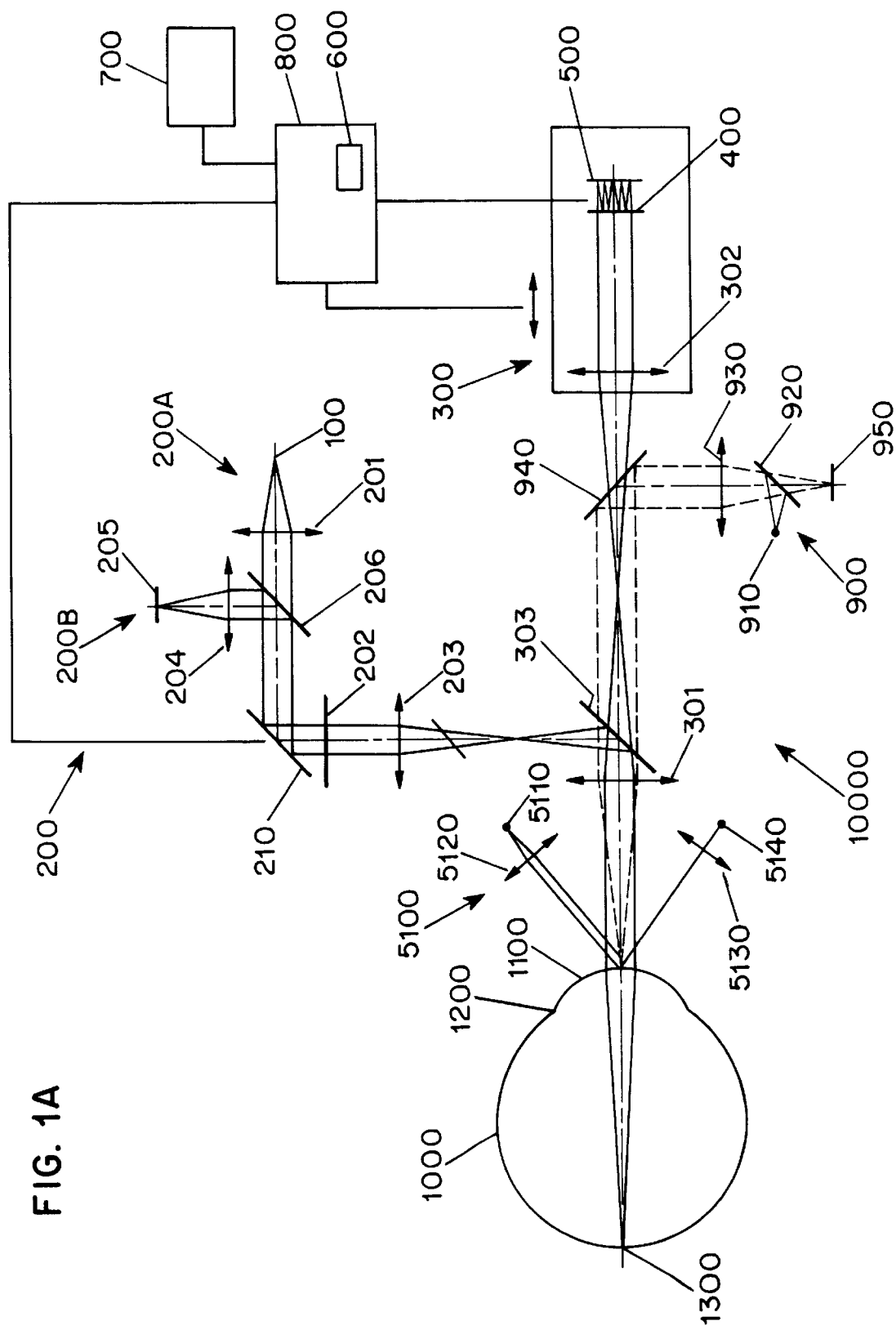
FIG. 1A is a block diagram of an optical characteristic measuring apparatus in a first embodiment according to the present invention.

Referring to FIG. 1A, an optical characteristic measuring apparatus 10000 according to a first embodiment of the present invention includes an illuminating light source 100; an illuminating optical system 200 for illuminating the retina of an eye to be examined via an illuminating state changing unit 210 capable of changing an illuminating state created by light rays emitted from the light source 100; a light receiving optical system 300 for receiving light rays reflected back from the retina of an eye to be examined and guiding the reflected light rays to a light receiving unit 500; a converting member 400 for separating the reflected light rays into at least seventeen regions, the member having an action of converging light rays in each of the regions and an action of allowing transmission of light rays in each of the regions; the light receiving unit 500 for receiving the light rays from the converting member 400; and an optical characteristic arithmetic unit 600 for determining optical characteristics of the eye on the basis of the inclination angle of the light rays which have been converged by the converting member 400 and then received by the light receiving unit 500. The above illuminating state changing unit 210 changes, on the basis of the optical characteristics obtained by the optical characteristic arithmetic unit 600, the illuminating state of the illuminating optical system 200 such that the illuminating optical system 200 illuminates a minute region on the retina of the eye.

The apparatus 10000 also includes a control means 800 for controlling the entire apparatus including the optical characteristic arithmetic unit 600.

It is desirable that the light source 100 is capable of emitting light having a high spatial coherence and a low temporal coherence. The light source 100 of the first embodiment is a SLD (Super Luminesent Diode), which is a point light source having a high luminance.

The light source 100 need not be limited to the SLD (Super Luminescent Diode); a laser which emits light having a high spatial coherence and a high temporal coherence can be employed as the light source 100 if a rotary diffuser or the like is inserted in an optical path to lower the temporal coherence properly.

Although both the spatial coherence and the temporal coherence of the light emitted by a light source such as LED as low, it can be used if a pinhole or the like is disposed at a position corresponding to the light source an the light path, provided that it emits a large quantity of light.

The wavelength of the light emitted by the illuminating light source 100 of the first embodiment may be equal to, for example, that of the E line at the middle of the visible region. Although it is desirable to use the e line (546.07 nm), which is a reference wavelength for spectacles, for measurement, the d line (587.56 nm) may be used for measurement when the optical characteristic measuring apparatus is used in the USA.

When the light source 100 is being switched on continuously, at the light receiving unit 500, the light rays for measuring the optical characteristics and the light rays of the front eye part of the eye to be examined, i.e. the object to be examined, are received at the same time.

Also, when the light source 100 is flashed on and off, at the time of extinguishing the light source, an image of only the front eye part of the eye to be examined is formed at the light receiving unit 500, and at the time of switching on the light source, the light rays for measuring the optical characteristics are received at the receiving, unit 500.

This makes it possible to form the image of the eye part of the eye to be examined, i.e. the object to be examined, which contains no light rays for measuring the optical characteristics, This situation can be said to be more desirable.

The illuminating optical system 200 illuminates the retina of an eye to be examined with light rays emitted from the light source 100. The illuminating optical system 200 includes a first condenser lens 201, the illuminating state changing unit 210, a variable diaphragm 202, a second condenser lens 203, a fixation point focusing lens 204, and a fixation point 205.

The illuminating state changing unit 210 changes an illuminating state created by light rays emitted from the light source 100.

Figure 8:
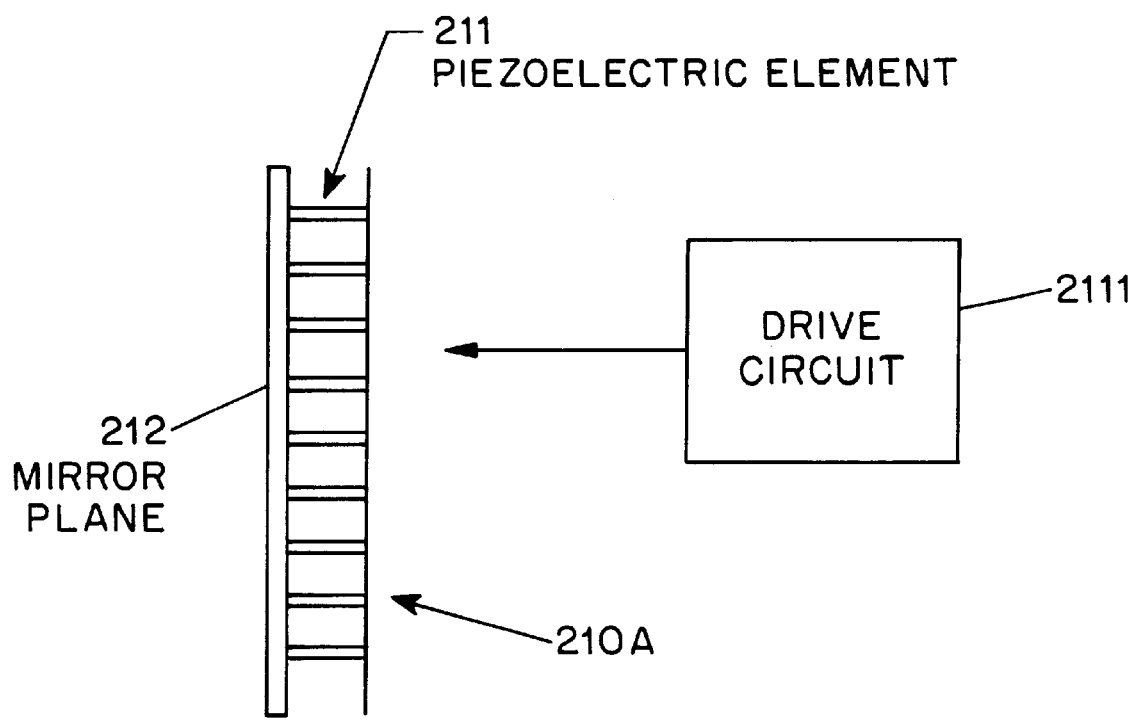
FIG. 8 is a diagram illustrating an illuminating state changing unit.

The illuminating state changing unit 210 in the first embodiment is composed of a deformable mirror 210A shown in FIG. 8

The deformable mirror 210A includes a mirror plane 212 and a piezoelectric element 211, wherein the mirror plane 212 is deformed by applying a drive voltage from a drive circuit 2111 to the piezoelectric element 211, to thereby change the illuminating state.

The illuminating state changing unit 210 is not limited to the deformable mirror 210A. For example, as the illuminating state changing unit 210, there may be used a spatial light modulator made from liquid crystal or the like, or a lens system including a cylindrical lens which is, for example, composed of a combination of a cylindrical lens and a spherical lens.

Figure 1B:
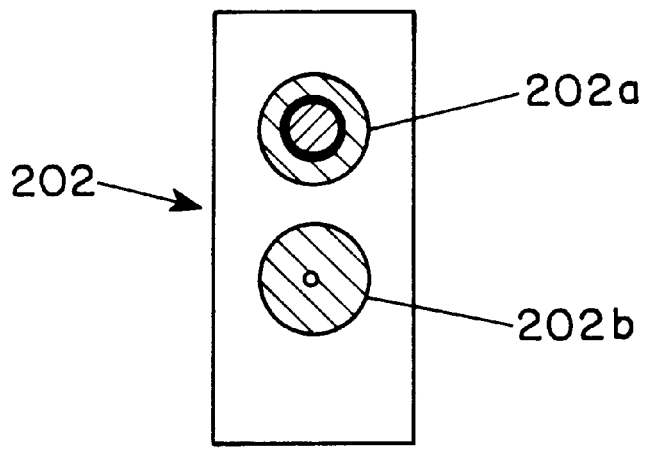
FIG. 1B is a front view of a variable diaphragm included in the optical characteristic measuring apparatus of FIG. 1.

The variable diaphragm 202 is a light screening member. As shown in FIG. 1B, the variable diaphragm 202 is provided with a first diaphragm 202a having an aperture in its peripheral portion, and a second diaphragm 202b having an aperture in its central portion. The first diaphragm 202a and the second diaphragm 202b are arranged side by side. The variable diaphragm 202 is moved in directions perpendicular to its optical axis by a signal provided by the controller 800 to dispose either the first diaphragm 202a or the second diaphragm 202b on the optical path.

Accordingly, the variable diaphragm 202 of the illuminating optical system 200 is able to create a first illuminating state for illumination through a region around the center of the pupil of the eye 1000 and a second illuminating state for illumination through the periphery of the pupil of the eye 1000 at a point substantially conjugate with the pupil of the eye 1000.

The eye 1000 has the cornea 1100, the iris 1200 and the retina 1300.

The variable diaphragm 202 reduces the influence of light reflected by the cornea on measurement.

The reflected light guiding optical system 300 guides the light rays reflected from the retina 1300 of the eye 1000 to the light receiving device 500.

The light receiving optical system 300 includes an objective lens 301, a relay lens 302, the converting member 400 for converting reflected light rays into at least seventeen beams, and a beam splitter 303. The light receiving device 500 of the reflected light guiding optical system 300 is conjugate with the variable diaphragm 202 of the illuminating optical system 200. The light receiving device 500 and the variable diaphragm 202 are conjugate with the iris 1200.

The light reflected from the cornea can be prevented from affecting the measurement of refraction by using a screened portion of the illuminating optical system 200 for the measurement of refraction.

If the first diaphragm 202a of the variable diaphragm 202 is on the optical path, a region corresponding to the central screening portion of the first diaphragm 202a is measured. If the second diaphragm 202b is disposed on the optical path, a region corresponding to a portion around the central aperture is measured.

In addition, if it is allowed to slightly sacrifice the measurement range near the periphery of the pupil of the eye, the measurement can be performed not by use of the variable diaphragm mechanism but by use of only the second diaphragm for illumination through a portion near the periphery of the pupil of the eye.

The illuminating optical system 200 is constructed so that a minute region on the eyeground of the eye 1000 is illuminated by the light emitted by the light source 100 according to the refracting power of the eye 1000. The abnormal refraction of the eye 1000 can be corrected by moving a point light source illuminating system 200A for projecting the light emitted by the light source 100, and an elluminating system including a fixation point projecting system 200 B.

The point light source illuminating system 200A comprises the First condenser lens 201, the variable diaphragm 202 and the second condenser lens 203. The fixation point projecting system 200B comprises the fixation point focusing lens 204 and the fixation point 205. Light rays emitted by the point light source illuminating system 200A and light rays emitted by the fixation point projecting system 200B are combined in coaxial light rays by a beam splitter 206.

The conjugate relationship between the light source 100 and the fixation point 205 is maintained. The illuminating optical system 200 is moved to form images of the point light source and the fixation point 205 an the retina 1300, and then the fixation point projecting system 200B is moved slightly away from the beam splitter 220 by a signal provided by the controller 800 to blur the image of the fixation point 205.

A first diopter adjusting mechanism adjusts the diopters of the point light source illuminating system 200A and the fixation point projecting system 200B by moving the variable diaphragm 202 and the fixation point 205 respectively along their optical axes so that the level of light received by the light receiving device 500 is kept at a maximum.

One of the objects of the optical characteristic measuring apparatus 10000 in the first embodiment is the measurement of optical characteristics in a state having a specific refractive power at the far point of accommodation, the near point of accommodation or a point between the far point of accommodation and the near point of accommodation.

Accordingly, a minute region on the eyeground is illuminated with light rays according to the variation of the refractive power of the eyes 1000 because, in measurement at the far point of accommodation, for instance the refraction powers of the eyes 1000 vary in the range of −25D to 25D (Diopter). Therefore, the light source 100, the point light source illuminating system 200A and the fixation point projecting system 200B are moved by signals provided by the controller 800.

The light receiving optical system 300 includes an objective lens 301, a relay lens 302, the converting member 400, and a light receiving device 500. When an eye to be examined is located at a position separated an appropriate operational distance from the light receiving optical system 300, the light receiving optical system 300 satisfies the following relationship with the eye.

Namely, a front side focus of the objective lens 301 substantially coincides with a front eye parts of the eye to be examined, i.e. an object to be examined. Moreover, the front eye part of the eye to be examined is substantially in a conjugate relationship with the light receiving device 500 through the objective lens 301 and the relay lens 302.

The illuminating optical system 200 and the light receiving optical system 300 are configured as follows. Assuming that light rays emitted from the light source 100 are reflected at points at which the light rays are gathered, the illuminating optical system 200 and the light receiving optical system 300, maintaining a relation that a signal peak by the reflected light rays becomes its maximum at the light receiving unit 500, move in a coupled manner, move towards a direction in which the signal peak by the reflected light becomes stronger at the light receiving unit 500, and stop at a position at which the intensity becomes its maximum. This eventually allows the light rays from the light source 100 to be gathered on the eye to be examined.

The converting device 400 will be described hereinafter. The converting device 400 included in the reflected light guiding optical system 300 is a wavefront converting device which converts the reflected light rays into a plurality of light beams. The converting device 400 has a plurality of micro Fresnel lenses arranged in a plane perpendicular to the optical axis.

The micro Fresnel lens will be described in detail.

A micro Fresnel lens is an optical element having annular bands at height pitches for wavelengths and an optimized blaze at a focal point. A micro Fresnel lens which can be applied to the present invention has, for example, eight levels of optical path differences produced by semiconductor fine processing techniques, and is capable of achieving focusing at a focusing efficiency of 40% both for a zero-order light and for a first-order light.

As a result, launched into the light receiving unit 500 are a first-order light provided by a micro Fresnel lens corresponding to the converting member 400 as light rays indicating optical characteristics of the eye to be examined, and a zero-order light provided by the micro Fresnel lens as an image of the front eye part of the eye to be examined.

When the light source 100 is being switched on continuously, received at the same time at the light receiving unit are the light rays for measuring the optical characteristics and the light rays of the front eye part of the eye to be examined, i.e. the object to be examined. Accordingly, the image of the front eye part of the eye to be examined, i.e. the object to be examined, is formed on a display unit 700 in a state in which the points, at which the light rays for measuring the optical characteristics are gathered, are contained discretely.

Also, when the light source 100 is flashed on and off, an image of only the front eye part of the eye to be examined, at the time of extinguishing the light source, is formed at the light receiving unit and is displayed by the display unit 700. During a time period when the optical characteristics are being measured, the image of the front eye part of the eye to be examined can also be displayed by storing it in a buffer memory.

This makes it possible to form the image of the front eye part of the eye to be examined, i.e. the object to be examined, which contains no light rays for measuring the optical characteristics. This situation can be said to be more desirable.

Meanwhile, reflected light rays from eyegrounds pass through the objectivelens 301 and the relay lens 302, and are gathered on the light receiving unit 500 as the first-order light thereof through the converting member 400. Here, the zero-order light corresponds to transimitting light rays and the first-order light corresponds to converging light rays.

Also, the converting member 400 can be configured by a micro lens part for performing the converging operation and an aperture part for performing the transmitting operation in each region of the reelected light rays separated into at least five regions.

The converting member 400 according to the present first embodiment is constituted by a wave front convertng member for converting the reflected light rays into at least seventeen or more of light beams.

The light receiving device 500 receives a plurality or light beams prom the converting device 400. In the first embodiment, the light receiving device 500 is a CCD. The CCD may be a common CCD for TV use or a CCD having 2000×2000 elements for measurement use.

Although a CCD for TV use as the light receiving device 500 has a low resolution, the CCD for TV use is inexpensive and its output can be easily given to a personal computer which is used generally for image processing. NTSC image signals provided by a CCD and its driver can be easily given to a personal computer through an NTSC image input port.

Although a CCD for measurement use having 2000×2000 elements is expensive, analog signals representing measured values can be given to a personal computer it a CCD for measurement use is employed.

Signals provided by a COD can be converted into corresponding digital signals, and the digital signals may be given to a personal computer.

The reflected light guiding optical system 300 establishes substantially conjugate relationship between the iris 1200 of the eye 1000 and the converting device 400.

The beam splitter 303 is inserted in the reflected light guiding optical system 300 to direct the light transmitted by the illuminating optical system 200 toward the eye 1000, and to transmit the reflected light.

An XY alignment optical system 900 will be described below.

The XY alignment optical system 900 includes an alignment light source 910, a second beam splitter 920, an lens 930, and a third beam splitter 940.

An alignment light receiving unit 950 in the first embodiment is composed of a two-dimensional CCD which is, however, may be replaced with any light receiving device.

A Z alignment optical system 5100 comprises a fourth light source 5110, a collimator lens 5120, a condenser lens 5130 and a linear imaging device 5140.

The Z alignment optical system 5100 makes a point source coincide with a point near the vertex of the cornea 1100.

The linear imaging device 5140 is a linear PSD, but may be an imaging device of any suitable type.

The Z alignment optical system 5100 collimates light rays emitted by the fourth light source 5110 and illuminates the cornea 1100 with parallel light rays. The linear imaging device 5140 is disposed at a point to receive light rays reflected by regular reflection on a plane including an illumination optical axis and a reflection optical axis.

The Z alignment optical system 5100 is disposed so that the parallel light rays intersects the optical axis of the collimator lens 5120 when positioned at a predetermined distance.

The operation of the XY alignment optical system 900 will be described with reference to FIG. 10. An alignment light source 910 is turned on instep S1. The objective lens 930 focuses light rays on the cornea 1100 in step S2. The position of a bright point is observed by the alignment light receiving unit in step S3. Data is displayed on a monitor in steo S4 it manual alignment is selected. Data is sent to the control unit in step S5 if automatic alignment is selected.

The operation of the Z alignment optical system 5100 will be described with reference to FIG. 11. The fourth light source 5110. is turned on in step S1. Light rays are collimated by the collimator lens 5120 and a portion of the eye 1000 around the vertex of the cornea 1100 is illuminated with parallel light rays in step S2. A virtual image is formed in step S3, and the virtual image is projected on the linear imaging device 5140 by the condenser lens 5130 in step S4. The linear imaging device 5140 provides measured data on the position of the virtual image in step S5 and sends the measured data on the position of the virtual image to the control unit in step S6.

Alignment will be described in detail with reference to FIG. 12.

Suppose that the lenses on the eye side of the movable lens of the reflected light guiding system form a objective lens group. Alignment can be achieved by disposing the objective lens group so that the front focal point of the objective lens group coincide with a reference measuring plane of a front portion of the eye 1000 (exit pupil, the surface of the cornea).

The movable lens moves so that the front focal point of the movable lens coincides with a point where the measuring light rays traveled through the objective lens group intersect the optical axis. (The point is substantially conjugate with the center of curvature of the cornea 1100 when the shape of the cornea 1100 is measured, and is substantially conjugate with the eyeground when the optical characteristics are measured.) Consequently, substantially parallel light rays fall always on the light receiving device and a measuring region on the reference measuring plane can be substantially fixed.

The accurate position of the light rays on the reference measuring plane of the front portion of the eye 1000 can be determined by measuring the coordinates of the light rays at a point conjugate with the reference measuring plane of the front portion of the eye 1000 after the movable lens on the basis of data on the position at which light rays fall on the light receiving device by interpolation or extrapolation, and dividing the coordinates of the light rays by the lateral magnification of the optical system.

The principle of operation of the optical characteristic calculating unit 600 which calculates the optical characteristics of the eye 1000 on the basis of the inclination of light rays determined by the light receiving device 500 will be described hereinafter.

"No relay lens and immovable: Optical characteristics including spherical component are measured"

Emmetropia: Parallel light rays are focused on the eyeground to make a secondary light source on the eyeground emit parallel light rays.

Myopia: Convergent light rays are emitted.

Regular astigmatism: Astigmatism is measured.

Irregular astigmatism: High-order aberration is mixed.

A method of calculation will be described in detail.

Figure 2:
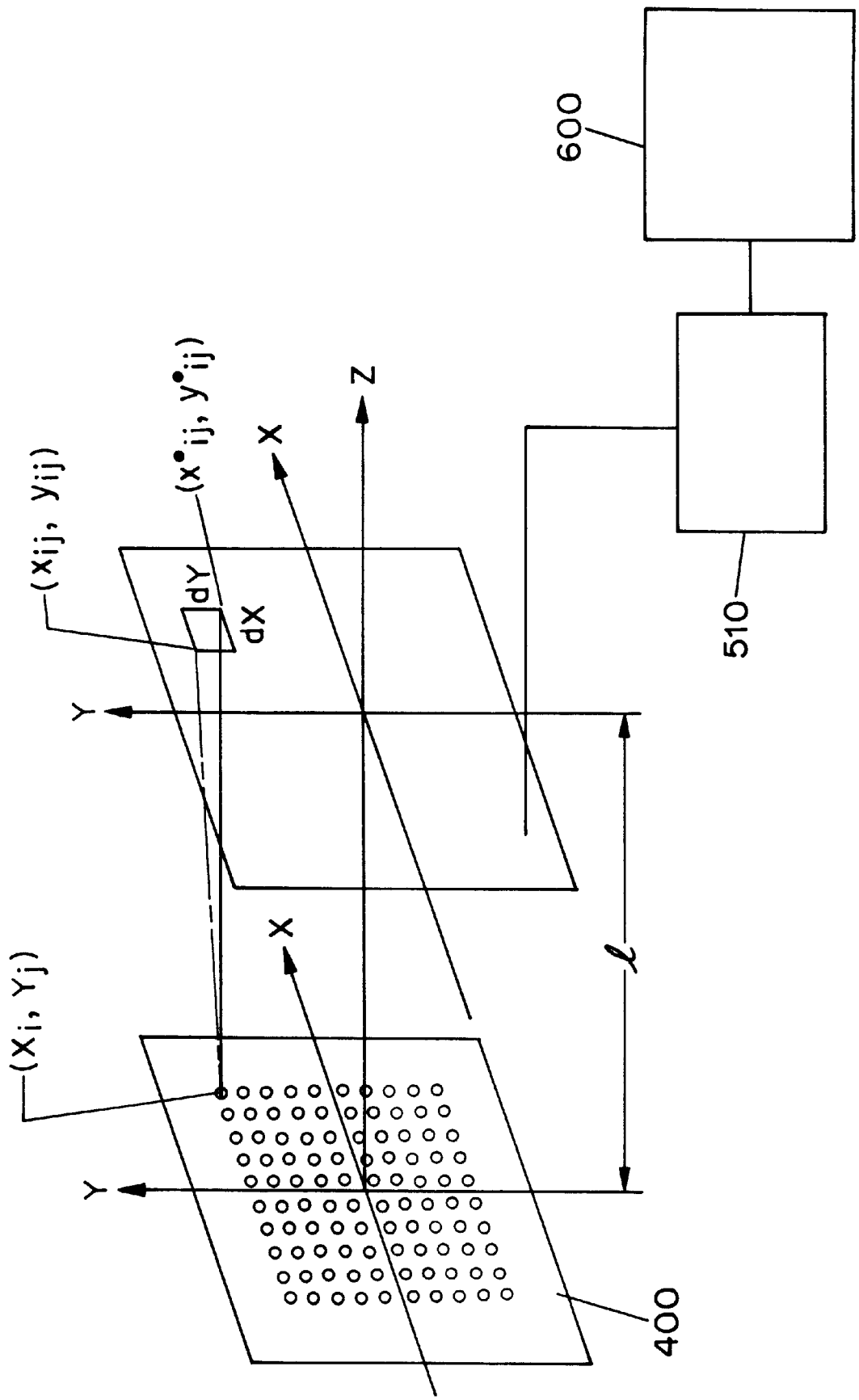
FIG. 2 is diagrammatic view of assistance in explaining the principle of the optical characteristic measuring apparatus of FIG. 1.

As shown in FIG. 2, coordinate axes X and Y are set on the converting device, and coordinate axes x and y are set on the light receiving device 500. Then, a wave surface is expressed by a polar coordinate system or a rectangular coordinate system:

$$w(r, \theta) = W(X, Y) \tag{1}$$

The (i, j)-th measured data is expressed by:

$$w(r_i, \theta_j) = W(X_i, Y_j) \tag{2}$$

The contents of the measured data will be explained later.

The wave surface is expressed by an approximate expression:

$$F(K, G, T, S, C, A, X, Y) = \text{Constant (K)} + \text{Inclination (G, T, X, Y)} + \text{Spherical surface (S, X, Y)} + \text{Regular astigmatism (C, A, X, Y)} \tag{3}$$

The components of this polynomial will be explained.

The constant term is K.

The inclination reflecting alignment error is:

$$G r \cos(\theta - T) = G \cos(T) X + G \sin(T) Y \tag{4}$$

Spherical surface (Discussion concerning sign)

$$S \pm \sqrt{S^2 - r^2} = S \pm \sqrt{S^2 - (X^2 + Y^2)} \tag{5}$$

Sign is "+" when S is negative and sign is "−" when S is positive.

Regular astigmatism (Discussion concerning sign)

$$\left(C^2 \pm \sqrt{C^2 - r^2}\right)\cos^2(\theta + A) = \left(C \pm \sqrt{C^2 - (X^2 + Y^2)}\right) \tag{6}$$

$$\left(\frac{\cos^2(A)X^2 + 2\sin(A)\cos(A)XY + \sin^2(A)Y^2}{X^2 + Y^2}\right)$$

Formula 2

Sign is "+" when C is negative and sign is "−" when C is positive.

The square sum of the residuals at each measurement point is:

$$\sum_{i,j} [W(X_i, Y_j) - F(K, G, T, S, C, A, X_i, Y_j)]^2 \qquad (7)$$

Values of K, G, T, S, C and A are determined so that a value calculated by Formula 3 is a minimum. The suffixes i and j denotes one of the elements of the converting device 400. Practically, the data represents inclinations and hence the derivative of each wave surface is used for calculation because data measured by the optical characteristic measuring apparatus are the inclination of light rays.

The inclination of light rays can be directly determined by the differentiation of the wave surface by positional coordinates. Values measured by the wavefront sensor are transverse aberrations from a reference.

It is generally known that the following relation holds approximately in FIG. 2.

$$\frac{\partial W(X,Y)}{\partial X} = \frac{dx(X,Y)}{l} \qquad (8)$$

$$\frac{\partial W(X,Y)}{\partial Y} = \frac{dy(X,Y)}{l} \qquad (9)$$

where l is the distance between the converting device 400 and the light receiving device 500. "Wave surface, and transverse aberration measured by the wavefront sensor"

Values dx(X, Y) and dy(X, Y) are calculated for each element of the converting device 400, having a center point at X, Y, in which dx and dy are distances along the x-axis and the y-axis between a predetermined origin on the light receiving device 500, and a point on the light receiving device 500 where the light beam falls on the light receiving device 500. As shown in FIG. 2, an origin corresponding to one element of the converting device 400 is a point on the light receiving device 500 where the converted light rays can be measured when both the spherical component and the astigmatism component representing the refractive characteristic of the eye are 0 diopter, and there is no residual of irregular astigmatism, which will be described later.

Suppose that the position of each point is $(x^0, y^0)$ when S, C and A are zero and there is no residual aberration. Then, $$dx(X_i, Y_j) = x_{ij} - x^0_{ij} \qquad (10)$$

$$dy(X_i, Y_j) = y_{ij} - y^0_{ij} \qquad (11)$$

Therefore, at the time of using the differentiation, the square sum of the the residuals is:

$$\sum_{i,j}\left[\left\{\frac{dx(X_i, Y_j)}{l} - \left(\frac{\partial F}{\partial X}\right)_{(X_i, Y_j)}\right\}^2 + \left\{\frac{dy(X_i, Y_j)}{l} - \left(\frac{\partial F}{\partial Y}\right)_{(X_i, Y_j)}\right\}^2\right] \qquad (12)$$

The parameters G, T, S and C of F which makes the residual a minimum may be determined by an appropriate nonlinear optimizing method, such as a method of damped least squares.

The values of K, G and T are considered to reflect measuring errors. In an auto-refractometer, S, C and A are measured values.

Although signs of some terms in the expressions expressing a spherical surface and regular astigmatism are indefinite, combinations may be calculated individually and a case where the residual is the smallest may be employed.

A Irregular Astigmatism Component

The differentiation residuals are irregular astigmatism component.

The conventional auto-refractometer is unable to measure the residual component, and a new piece of software is necessary.

When analyzing the residual, i.e., the irregular astigmatism component, (1) The residual is calculated and represented in the form of the square sum.

(2) The residual is divided into components by a method similar to a method known in the aberration theory.

(3) All the deviations from the wave surface expressed by S, C and A as a reference surface are provided.

In some cases, a reference wave surface expressed by S or a reference wave surface represented by a plane is necessary to find out the distortion of the wave surface if the irregular astigmatism is large.

"Square Sum of Residuals"

The square sum of residuals is measured by using K, G, T, S, C and A determined by the foregoing method. If the square sum of residuals has N rows and M columns, a measurement value of the square sum of residuals is obtained by dividing the square sum of residuals by a value obtained by doubling the square of n=N×M.

$$\frac{\sum_{i,j}\left[\left\{\frac{dx(X_i, Y_j)}{l} - \left(\frac{\partial F}{\partial X}\right)_{(X_i, Y_j)}\right\}^2 + \left\{\frac{dy(X_i, Y_j)}{l} - \left(\frac{\partial F}{\partial Y}\right)_{(X_i, Y_j)}\right\}^2\right]}{2n} \qquad (16)$$

B Analysis of Components

Comatic aberration: $r^{(2n+1)}\cos(\theta+T_n)$ (n=1, 2, ...)

Spherical aberration: $r^{2n}$ (n=2, 3, ...)

High-order astigmatism: $r^{2n}\cos^2(\theta+A_n)$ (n=1, 2, ...)

There is an important aberration of an order higher than that of the astigmatism component in the direction of rotation $f(r)\cos^n(\theta+T_n)$ (n=3, ...)

The parameters of these terms are determined by subtracting values contributed to the components of the inclination, the spherical surface and the regular astigmatism by G, T, S, C and A obtained previously from the inclination of light rays. The comatic aberration, the spherical aberration, the high-order astigmatism and other contribution can be calculated.

C Output of Deviation from Reference Wave Surface

A distance between corresponding positions on the reference wave surface $W_b$ and the actual wave surface $W_v$ is indicated.

In the following description, Fb and Fr are obtained by removing terms of constants and inclination from F.

These are expressed by functions approximating wave surfaces.

(Reference wave surface)=$W_b(X_i, Y_j)=F_b(S, C, A, X_i, Y_j)$ (Reconstructed wave surface)=$W_r(X_i, Y_j)=F_r(S, C, A,$ parameters of irregular astigmatism component, $X_i, Y_j)$ $$\Delta Z_{ij} = W_r(X_i, Y_j) - W_b(X_i, Y_j) \quad (17)$$

All the indications can be expressed in a unit of wavelength or a unit of micrometer.

D Indication of Deviation of Power from Reference Wave Surface (1) Power is calculated on the basis of the respective calculated residuals of the components.

(2) The inclination dependent only the residual component at that point is determined on the basis of only the residual component.

(3) The inclination at that point calculated on the basis of the reference wave surface Wb is subtracted from the measured value, and the power of a point is calculated on the basis of points, typically, eight or fifteen points, around the point.

As shown in FIG. 3, the power indicates directly a quantity and an orientation relating to the maximum and the minimum curvature at a point on a geometrical curved surface. When light rays converge in a radius R of curvature, power is expressed by 1/R.

Figure 4:
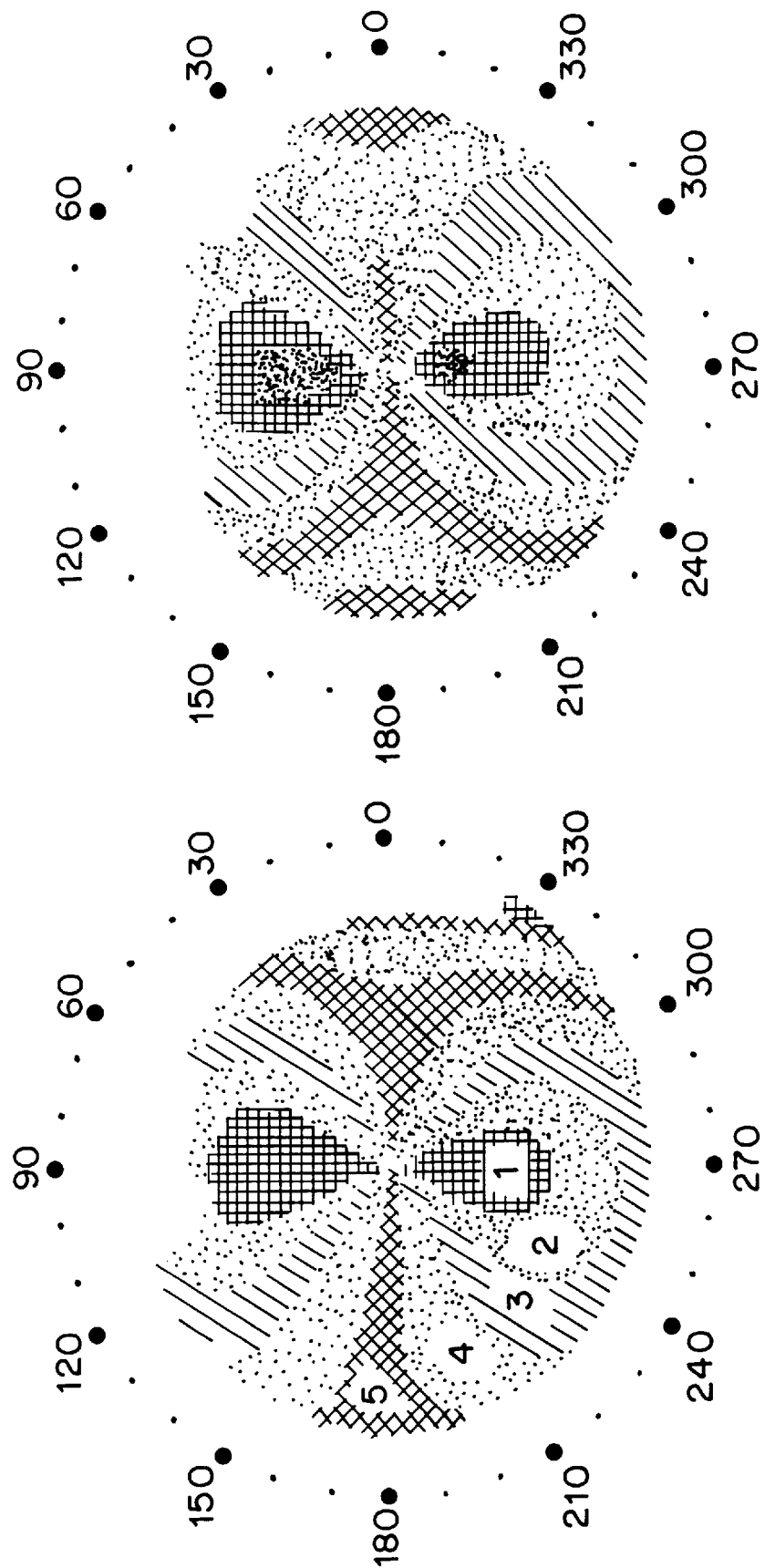
FIG. 4 is a pictorial view of assistance in explaining a method of indicating meridional power.
Figure 5:
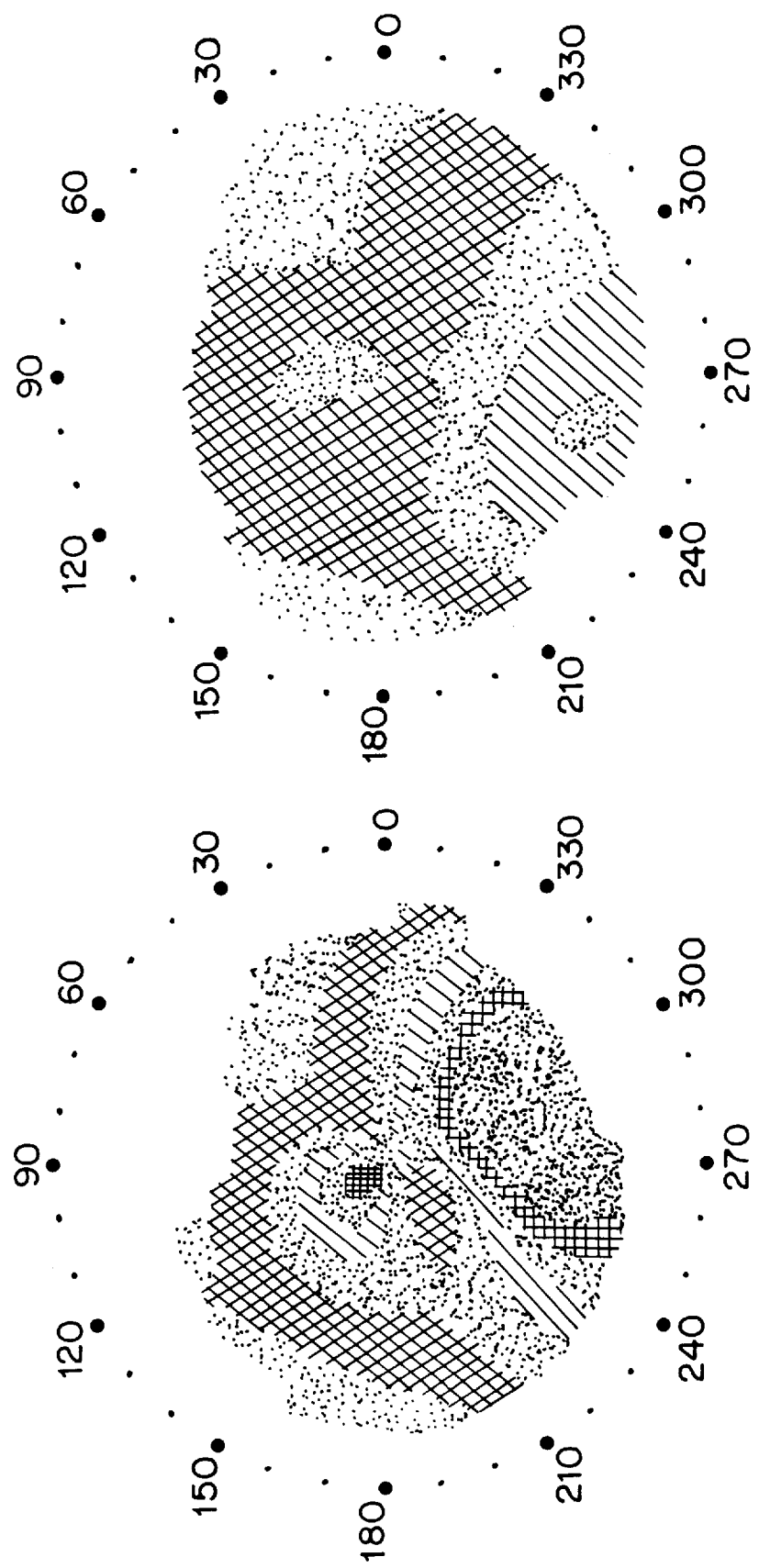
FIG. 5 is a pictorial view so assistance in explaining a method of indicating meridional power.

Meridional power is indicated by a method illustrated in FIGS. 4 and 5.

Generally, regular astigmatism has a high power in the direction of the vertical meridian and a low power in the direction of the horizontal meridian. Power is expressed in diopters.

The operation of the converting device 400 for converting the reflected light rays into at least seventeen light beams will be described in detail.

It is possible to calculate measurement values, as long as they are measurement values of the spherical component S, the cylindrical component C, and the axis angle component A, by using at least five points of data which consist of the point of origin and four points lying in different four radial directions. Moreover, if there is need of information on data which are at least one order higher than the five points of data, the number of the measuring points, through a summation of 2*8=16 and the point of origin, turns out to be at least seventeen or more.

Accordingly, the optical characteristic calculating unit 600 determines the inclination of light rays from a position on which the primary light rays are converged by the plurality of micro Fresnel lenses, and determines the optical characteristics of the eye 1000 on the basis of the inclination of light rays.

A blurred image is formed at one point represented by data on received light rays if the converting device 400 does not use the micro Fresnel lenses, and hence the center of gravity of each point is determined.

Figure 6:
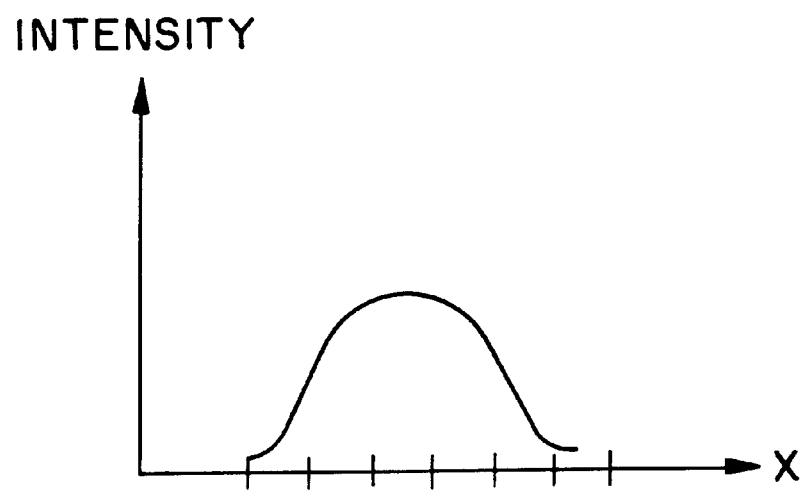
FIG. 6 is a graph of assistance in explaining a method of improving the accuracy of position measurement.

Even if micro Fresnel lenses are used, the accuracy of position measurement can be increased by observing an image intentionally blurred by the light receiving elements as shown in FIG. 6. The position of the center of gravity can be determined by making the projected light rays fall on a plurality of pixels on the light receiving surface and making reference to the intensities of light rays fallen on the pixels.

The accuracy of position measurement not higher than 1/10 of the element can be secured by thus calculating the position of the center of gravity.

The optical characteristic measuring apparatus may be provided with a display unit 700 for displaying the results of arithmetic operations carried out by the optical characteristic calculating unit 600.

The display unit 700 are capable of displaying the optical characteristics of the eye 1000 in the spherical component, the regular astigmatism component, the angle of the axis of the regular astigmatism component, and the irregular astigmatism component, which are determined by calculation by the optical characteristic calculating unit 600.

Examples will be given below.

(1) Display of Irregular Astigmatism Component

The irregular astigmatism component indicates a comatic component, a spherical aberration component and a high-order astigmatism component.

(2) Display of Irregular Astigmatism Component as Deviation

The irregular astigmatism component indicates two-dimensionally deviation from the wave surface consisting of only a spherical component and a regular astigmatism component.

(3) Two-dimensional Display of Curvature of Wave Surface in Diopters

Two-dimensional graphic display is possible. A point having astigmatism has two curvatures. According to the differential geometry theory, both are perpendicular to each other.

The display unit 700 is capable of graphically displaying the optical characteristics of the eye 1000. The display unit 700 is capable of displaying a picture of the eye 1000 viewed from the front on an x-y coordinate system and of mapping powers in, for example, diopters on an x-y coordinate system.

The display unit 700 is capable of displaying the deviations of the optical characteristics of the eye 1000 from those of the normal eye.

The display unit 700 is also capable of mapping the deviations from a reference wave surface reproduced from the calculated values of S, C and A on the order of wavelength on the x-y coordinate system.

The display unit 700 is capable of graphically displaying deviations of the optical characteristics of the eye 1000 from those of the normal eye, and those data can be represented in contour.

The display represented in contour can be mapped by, for example, pseudocolors.

Described next, based on FIG. 7(*a*) and FIG. 7(*b*), is an alignment.

Figure 7A:
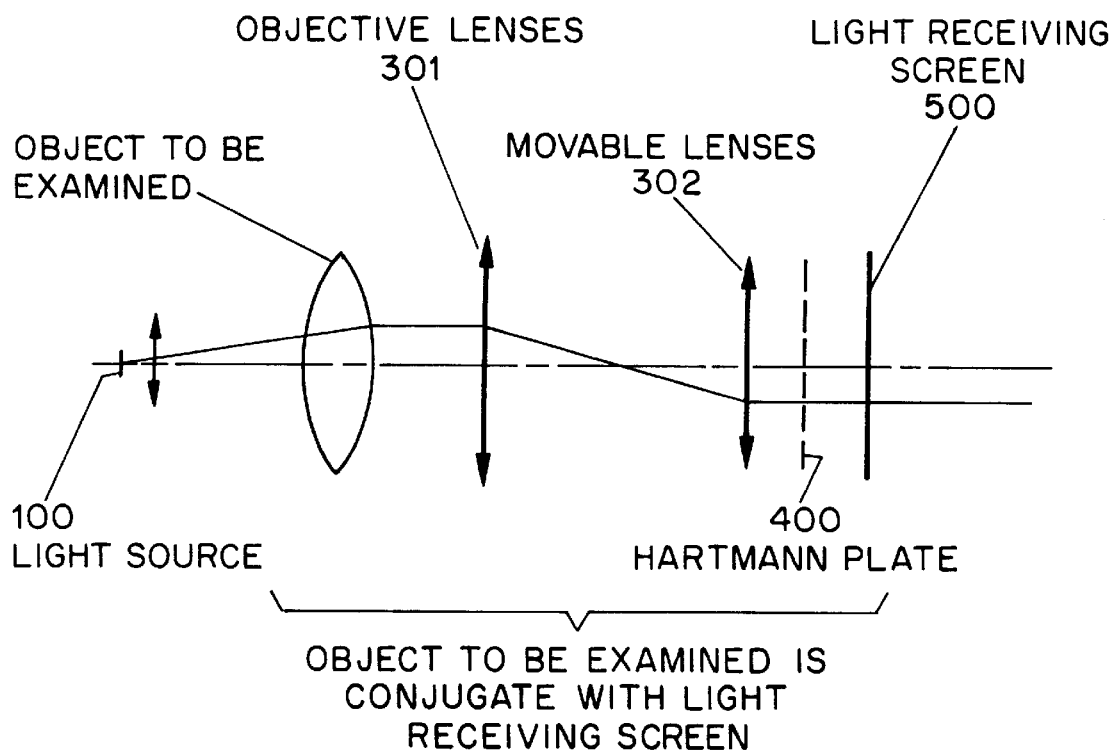
FIG. 7(A) and FIG. 7(B) are diagrams for explaining an alignment.
Figure 7C:
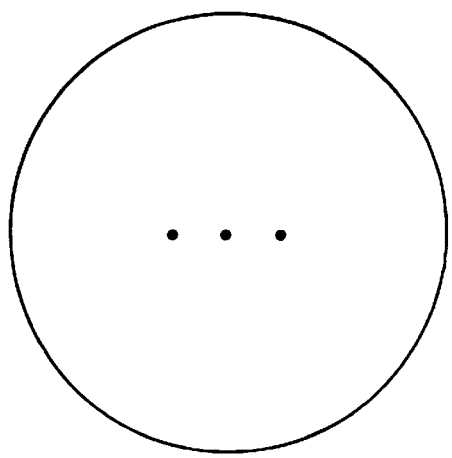
FIG. 7(c) is a diagram illustrating the alignment using a lens meter.
Figure 7B:
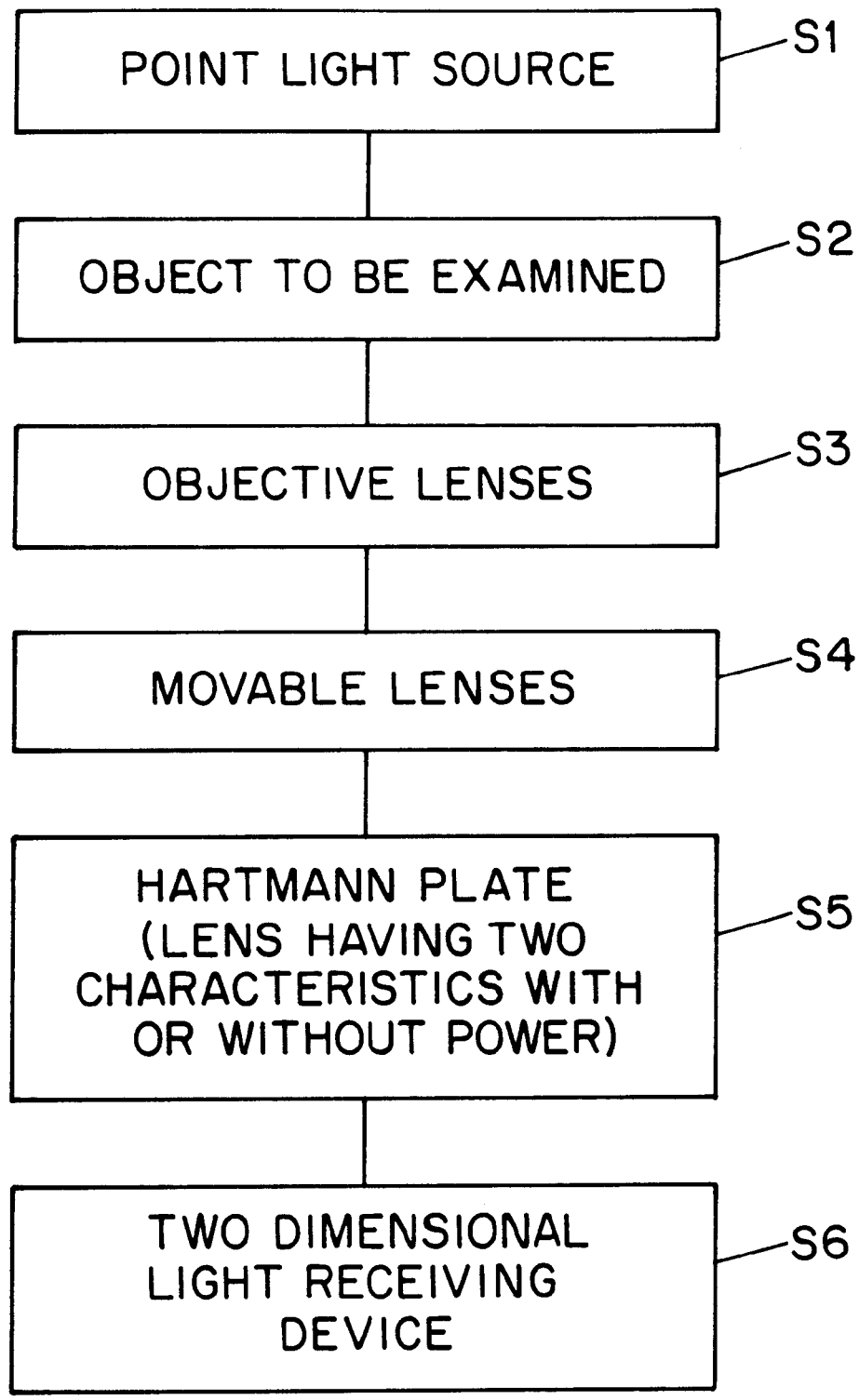

As shown in FIG. 7(*a*), if lenses, which exists at the side of a person to be examined with reference to movable lenses 302 in the light receiving system, are assumed to be objective lenses 301, the alignment can be achieved by locating the objective lenses 301 so that the front side focus thereof coincides with a measurement reference plane of the object to be examined (for example, an injection pupil or a cornea surface when the object to be examined is a human eye).

The movable lenses 302 moves so that a front side focus of the movable lenses 302 comes to a point (which turns out to be a substantially conjugate point with reference to eyegrounds when the object to be examined is the human eye) at which a measuring light beam, after having passed through the objective lenses 301, intersects the optical axis. This allows substantially parallel light rays to be always launched into the light receiving device 500, thus making it possible to make a measurement region at the measurement reference plane substantially unchanged.

When the object to be examined is, for example, the human eye, an accurate position of a measuring light beam at a measurement reference plane of the front eye part can be obtained as follows. Based on a position at which the light beam passes through the converting member 400 and a position at which the light receiving device 500 receives the light beam, using interpolation method or extrapolation method, the light beam coordinate is determined at a conjugate point of the measurement reference plane of the front eye part after the movable lenses have passed, and then the light beam coordinate determined is divided by a transverse magnification of the optical system, thus obtaining the accurate position.

Described below, based on FIG. 7(*b*), is the operation.

At S1 (step 1, hereinafter abbreviated as S1), the light source 100 is switched on. Then, at S2, an object to be examined is fixed. Next, at S3, a front side focus position of the objective lenses 301 is made to coincide with the object to be examined. Still next, at S4, the movable lenses 302 are caused to move so that a front side focus of the movable lenses 302 coincides with an image of the light source 100. Moreover, at S5, the image is formed by making use of a zero-order light and a first-order light provided by the micro Fresnel lens (Hartmann plate) 400. Finally, at S6, the image formed at S5 is received, using a two dimensional light receiving device which is equivalent to the light receiving unit 500.

Additionally, as shown in FIG. 7(C), in the case of a lens meter, there is an effect of achieving the alignment with the use of marked points.

In the present first embodiment, the description is given taking a human eye as an object to be examined. The object to be examined, however, is not at all limited to the human eye, and the first embodiment makes it possible to measure optical characteristics of any object that is to be examined.

Furthermore, although the converting member 400 in the present first embodiment is configured to convert the reflected light rays into at least seventeen light beams, it is sufficient to employ a converting member which converts the reflected light rays into at least five light beams.

Figure 9:
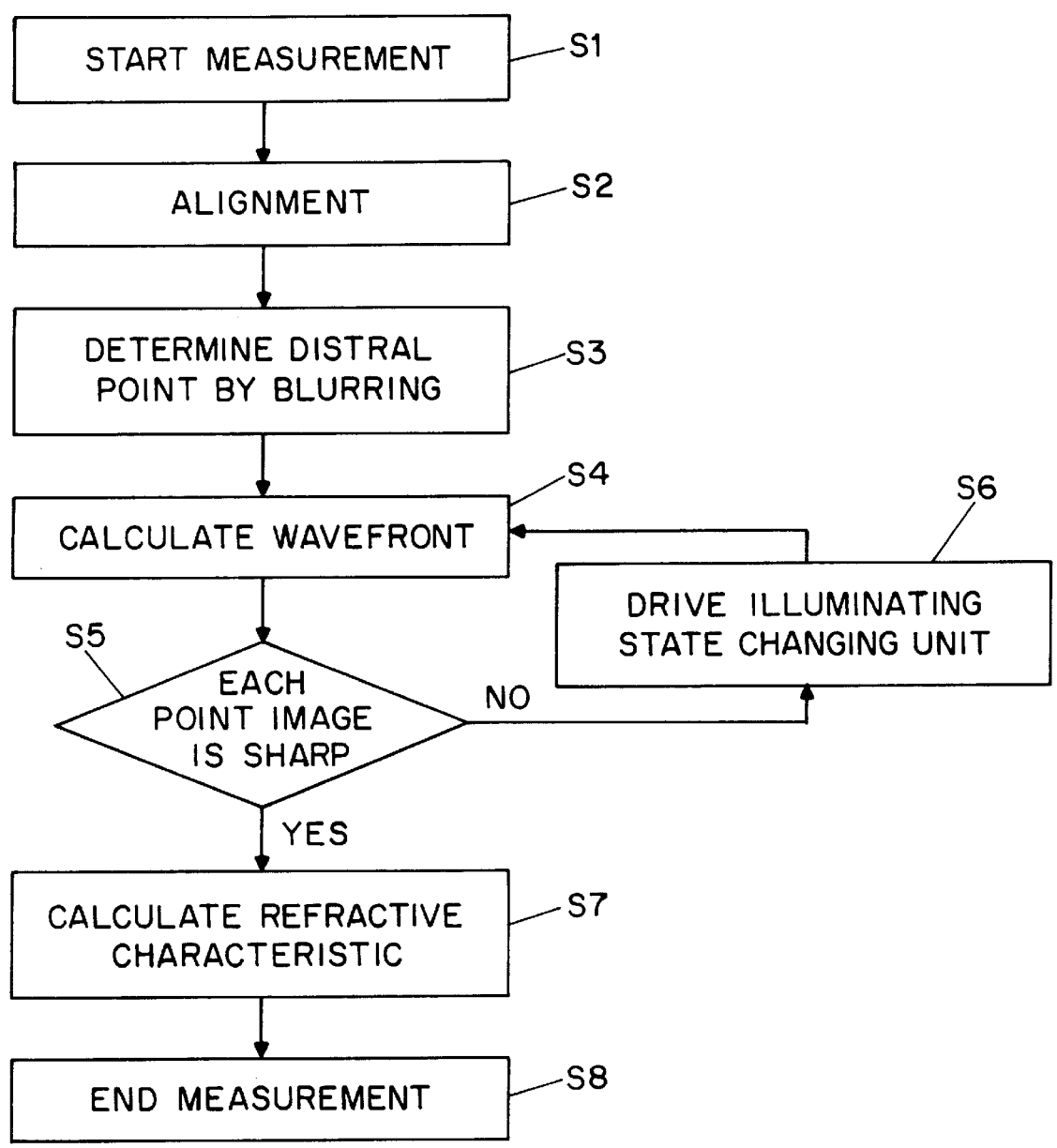
FIG. 9 is a block diagram illustrating measurement steps using the optical characteristic measuring apparatus according to the first embodiment.

Measurement steps using the optical characteristic measuring apparatus according to the first embodiment will be described in detail with reference to FIG. 9.

After measurement starts at step S1, alignment is carried out using the XY alignment optical system 900 and Z alignment optical system 5100 at step S2. At step S3, a distal point is determined by blurring to adjust the alignment such that a point image formed by the converting member 400 is sharply viewed. The above-described measurement of wavefronts is performed at step S4, and the process goes on to step S5. In addition, the wavefronts express the aberration of the eye to be examined.

At step S5, it is judged whether or not each point image formed by the converting member 400 is sharp, and if each point image is not sharp, the process goes on to step S6 at which the illuminating state changing unit 210 is driven to cancel the aberration of the eye.

After the aberration of the eye is canceled at step S6, the process is returned to step S4 at which the measurement of wavefronts is performed again.

If it is judged that each point image is sharp by the above feedback control at step S5, the process goes on to step S7 at which the above-described calculation of the refractive index is carried out. Then, at step S8, the measurement is ended.

This feedback control realizes a control system in which the control means 800 controls the illuminating state changing unit 210 to cancel the aberration component of the eye and subjects the response again to arithmetic processing, thereby compensating for the aberration component of the eye.

One example of the above control will be described below.

The optical characteristic arithmetic unit 600 determines wavefronts W ($X_i$, $Y_j$) of light rays reflected from the retina 1300 of an eye to be examined using the above-described Formula 2, the Zernike's polynomial or the like.

The converting member 400 is kept in an approximately conjugate relationship with the illuminating state changing unit 210. In this case, if the illuminating state changing unit 210 is configured by orthogonal reflection, the deformable mirror is moved for a movement amount d ($\alpha_i$, $\beta_j$) in order to correct the wavefronts W ($X_i$, $Y_j$) (that is, the aberration component of the eye to be examined) measured by the converting member 400.

Here, the movement amount d is expressed by d=(W($X_i$, $Y_j$))/(2×(2)$^{0.5}$), and a point ($\alpha_i$, $\beta_j$) is conjugate with a point ($X_i$, $Y_j$).

[Second Embodiment]

Figure 13:
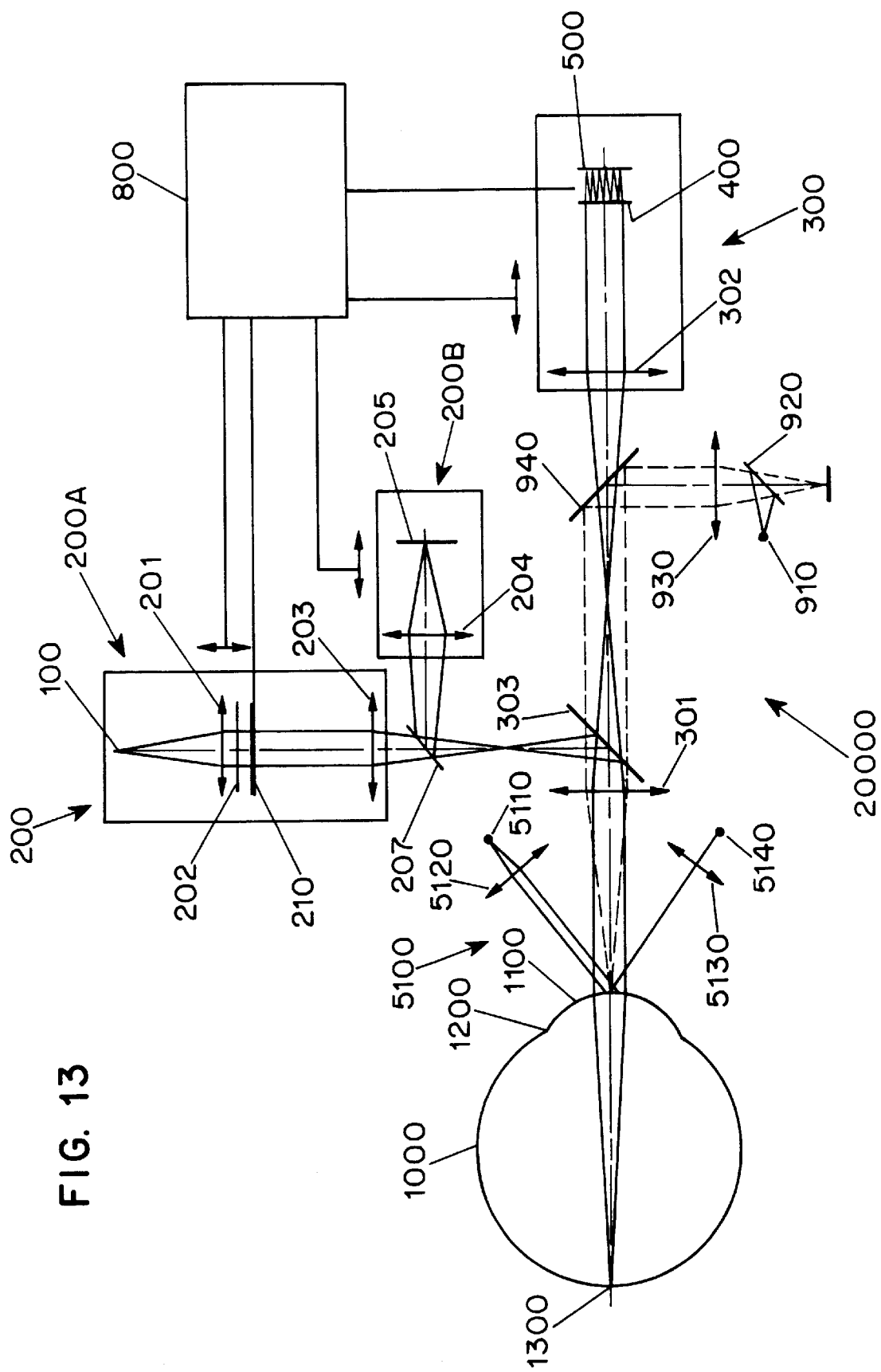
FIG. 13 is a diagram showing a configuration of an optical characteristic measuring apparatus according to a second embodiment of the present invention.

An optical characteristic measuring apparatus 20000 according to a second embodiment of the present invention has the same basic configuration as that of the apparatus 10000 according to the first embodiment except for an illuminating optical system 200 shown in FIG. 13. In this embodiment, therefore, only the illuminating optical system 200 will be described, and the explanation of the other composing elements being the same as those of the first embodiment is omitted.

The illuminating optical system 200 illuminates the retina of an eye to be examined with light rays emitted from a light source 100. The illuminating optical system 200 includes a first condenser lens 201, a variable diaphragm 202, an illuminating state changing unit 210, a second condenser lens 203, a fixation point focusing lens 204, and a fixation point 205.

The first condenser lens 201, variable diaphragm 202, and second condenser lens 203 constitute a point light source illuminating system 200A, and the fixation point focusing lens 204 and fixation point 205 constitute a fixation point projecting system 200B. Light rays from the point light source illuminating system 200A and light rays from the fixation point projecting system 200B are allowed to be coaxial with each other by means of a fourth beam splitter 207.

The light source 100 is kept in a conjugate relationship with the fixation point 205. After the illuminating optical system 200 is moved along the optical axis to form images of the point light source and the fixation point 205 on the retina, the fixation point projecting system 200B is moved slightly away from the beam splitter 207 on the basis of a signal from a control arithmetic means 800 to blur the image of the fixation point 205.

A first diopter adjusting mechanism adjusts the diopters of the point light source illuminating system 200A and the fixation point projecting system 200B so that the level of light received by a light receiving unit 500 is kept at maximum.

The other composing elements and effects of the optical characteristic measuring apparatus 20000 according to the second embodiment are the same as those of the apparatus 10000 according to the first embodiment, and therefore, the explanation thereof is omitted.

It should be noted that an object to be examined by the optical characteristic measuring apparatus of the present invention is not necessarily limited to an eye. That is to say, the measuring apparatus can be used for measuring optical characteristics of any object to be examined.

As described above, the optical characteristic measuring apparatus of the present invention having the above configuration includes an illuminating light source; an illuminating optical system for illuminating the retina of an eye to be examined via an illuminating state changing unit capable of changing an illuminating state created by light rays emitted from the light source; a light receiving optical system for receiving light rays reflected back from the retina of the eye and guiding the reflected light rays to a light receiving unit; and an optical characteristic arithmetic unit for determining optical characteristics of the eye on the basis of a signal outputted from the light receiving unit; wherein the illuminating state changing unit changes, on the basis of the optical characteristics obtained by the optical characteristic arithmetic unit, the illuminating state of the illuminating optical system such that the illuminating optical system illuminates a minute region on the retina of the eye, and accordingly, the apparatus exhibits an excellent effect of canceling the aberration of the eye and obtaining a clear image.

What is claimed is:

1. An optical characteristic measuring apparatus, comprising:

an illuminating light source;

an illuminating optical system for illuminating the retina of an eye to be examined via an illuminating state changing unit capable of changing an illuminating state created by light rays emitted from said light source;

a light receiving optical system for receiving light rays reflected back from the retina of the eye and guiding the reflected light rays to a light receiving unit; and an optical characteristic arithmetic unit for determining optical characteristics of the eye on the basis of a signal outputted from said light receiving unit;

wherein said illuminating state changing unit changes, on the basis of the optical characteristics obtained by said optical characteristic arithmetic unit, the illuminating state of said illuminating optical system such that said illuminating optical system illuminates a minute region on the retina of the eye.

2. The optical characteristic measuring apparatus according to claim 1, wherein said illuminating state changing unit comprises a deformable mirror.

3. The optical characteristic measuring apparatus according to claim 1, wherein said illuminating state changing unit comprises a spatial light modulator.

4. The optical characteristic measuring apparatus according to claim 1, wherein said illuminating state changing unit comprises a lens system including a cylindrical lens.

5. The optical characteristic measuring apparatus according to any one of claims 1 to 4, wherein the light receiving plane of said light receiving optical system is kept in an approximately conjugate relationship with the iris of the eye.

6. The optical characteristic measuring apparatus according to claim 5, wherein said light receiving optical system includes a converting member for separating the reflected light rays into at least seventeen regions, said member having an action of converging the light rays in each of the regions and an action of allowing transmission of the light rays in each of the light rays;

said light receiving unit receives the light rays from said converting member; and said optical characteristic arithmetic unit determines the optical characteristics of the eye on the basis of an inclination angle of the light rays which has been converged by said converting member and then received by said light receiving unit.

7. The optical characteristic measuring apparatus according to claim 6, wherein said converting member comprises a plurality of double-focus type micro Fresnel lenses arranged within a plane perpendicular to the optical axis; and said optical characteristic arithmetic unit calculates the inclination angle of the reflected light rays on the basis of the converged position on the light receiving plane of said light receiving unit, at which position the reflected light rays have been converged by said plurality of micro Fresnel lenses, and determines the optical characteristics of the eye on the basis of the inclination angle of the reflected light rays thus calculated.

* * * * *